United States Patent
Engelbrecht et al.

(10) Patent No.: US 7,631,782 B2
(45) Date of Patent: Dec. 15, 2009

(54) DISPENSING DEVICE FOR FLUID SUBSTANCES

(75) Inventors: Jurgen Engelbrecht, Hamburg (DE); Guido Meyer, Elmshorn (DE)

(73) Assignee: S&C Polymer Silicon-und Composite Spezialitaeten GmbH, Ellmshorn (DE)

( * ) Notice: Subject to any disclaimer, the term of this patent is extended or adjusted under 35 U.S.C. 154(b) by 396 days.

(21) Appl. No.: 10/539,112

(22) PCT Filed: Dec. 8, 2003

(86) PCT No.: PCT/EP03/13897

§ 371 (c)(1), (2), (4) Date: Jun. 16, 2005

(87) PCT Pub. No.: WO2004/054725

PCT Pub. Date: Jul. 1, 2004

(65) Prior Publication Data

US 2006/0071019 A1  Apr. 6, 2006

(30) Foreign Application Priority Data

Dec. 16, 2002  (DE) ................. 102 58 953

(51) Int. Cl.
*B67D 5/60* (2006.01)

(52) U.S. Cl. ............ 222/145.6; 222/137; 222/145.1; 222/145.5; 222/153.05

(58) Field of Classification Search ......... 222/137, 222/145.1, 145.6, 94, 325–326, 135, 567, 222/570, 145.5, 541.6, 153.05, 153.06

See application file for complete search history.

(56) References Cited

U.S. PATENT DOCUMENTS

| | | | |
|---|---|---|---|
| 3,179,107 A | * | 4/1965 | Clark .................. 604/242 |
| 3,532,316 A | | 10/1970 | Mathes |
| 4,261,481 A | | 4/1981 | Speer |
| 4,432,469 A | | 2/1984 | Eble et al. |
| 4,538,920 A | * | 9/1985 | Drake .................. 366/181.5 |
| 4,871,090 A | * | 10/1989 | Hoffmann ............... 222/81 |
| 4,974,756 A | * | 12/1990 | Pearson et al. ........... 222/562 |
| 4,978,336 A | * | 12/1990 | Capozzi et al. ............ 604/82 |
| 4,981,241 A | | 1/1991 | Keller |
| 5,370,273 A | | 12/1994 | Rohloff et al. |
| 5,746,414 A | * | 5/1998 | Weldon et al. ........... 251/149.6 |
| 5,775,541 A | * | 7/1998 | Perkins ................. 222/105 |
| 5,788,122 A | | 8/1998 | Keller |
| 5,918,772 A | | 7/1999 | Keller et al. |
| 6,161,730 A | | 12/2000 | Maeder et al. |
| 6,352,177 B1 | | 3/2002 | Bublewitz et al. |

FOREIGN PATENT DOCUMENTS

DE  880532  6/1988

\* cited by examiner

*Primary Examiner*—Frederick C. Nicolas
(74) *Attorney, Agent, or Firm*—Dennison, Schultz & MacDonald

(57) ABSTRACT

A dispensing device for fluid substances includes a receiving element for receiving fluid substances, formed of at least two rigidly interconnected containers with adjacent outlets on the front sides thereof, a mixing nozzle which is connected to the receiving element by a mixing nozzle holder and which is fluidically and conductively connected to the outlets, and a pressure-producing device for ejecting the fluid substances through the outlets. The mixing nozzle holder is a detachable catching closure.

8 Claims, 3 Drawing Sheets

DISPENSING DEVICE FOR FLUID SUBSTANCES

This application is a filing under 35 USC 371 of PCT/EP2003/013897 filed Dec. 8, 2003.

BACKGROUND OF THE INVENTION

The present invention relates in its generic type to a dispensing device for fluid substances. In particular it relates to a dispensing device which has a receiving element to receive fluid substances, having at least two containers which are fixedly connected to each other and have adjacent outlet orifices on the end face, a mixing nozzle which is connected to the receiving element by means of a mixing nozzle holder and is connected to the outlet orifices in a fluid-conducting manner, and a pressure-producing means for ejecting the fluid substances through the outlet orifices.

Dispensing devices such as these, which are used in particular for dental purposes, are known. Cartridges or double injection devices, for example, are used for mixing and for metered dispensing of dental multi-component materials and usually consist of two containers which are provided to receive two different substances. The containers are provided with outlet orifices on the end faces, which orifices are formed in such a way that mixing nozzles can be connected to them. The different components pressed out of the containers, for example, by stamping force meet in the mixing nozzle and exit this nozzle in the mixed state. After mixing, the mass hardens. This also applies to most of the residual quantity remaining in the mixing nozzle.

A device of this type is described in U.S. Pat. No. 4,767,026. In that case mixing nozzles are fixed in the manner of a bayonet connection to two holding elements by twisting over the outlet orifice of the containers. The disadvantage of this device is that the rotational movement of a mixing nozzle over the outlet orifices of the containers permits the components to contaminate each other and so permits hardening of the components in the outlet orifices and these outlet orifices can therefore become blocked.

An improved solution is a design in which the inlets of the mixing nozzles or of the outlet orifices of the containers are sufficiently separated from each other. This device is formed in such a way that the components only meet inside the mixing nozzle at a certain distance from the outlet orifices, which ensures that the hardening inside the nozzle remains restricted to a region sufficiently remote from the outlet orifices. In addition, this device permits a mixing nozzle, which is used to produce a mixture and which became unusable by reason of the hardening of its content, to be left as a quasi "temporary closure" of the outlet orifice on the containers until mixing is to take place using a newly fitted mixing nozzle.

A mixing nozzle of such a type is shown in U.S. Pat. No. 533,760. A bayonet closure is used but is rotatably held on the mixing nozzle so that after placing the nozzle on the outlet orifices of the containers only a holding ring is rotated which comes into positive-locking engagement in a pair of claws on the end face of the containers and therefore firmly holds the mixing nozzle. The ring is connected to the mixing nozzle in a complex manner and a relatively large number of rings are required, namely one per mixing nozzle.

This applies in a corresponding manner to another known arrangement (EP-A-730913) in which the bayonet coupling members are attached to the mixing nozzle housing in which an insert forming the inlet orifice of the mixing nozzle is contained so as to be rotatable relative to the housing.

A device in accordance with U.S. Pat. No. 4,753,536 consists of two containers fixedly connected to each other and containing the components, which containers have mutually adjacent outlet connection pieces on the end face. A mixing nozzle can be placed onto the outlet connection pieces and is to be secured in this position by a coupling device. The coupling device has a coupling plate which is supported by the outlet connection pieces and forms a guide extending transverse to the direction of the outlet connection pieces for two coupling slides. These can be displaced oppositely to each other on the guide into a closed position and support coupling strips which, in the closed position, each engage through 180° over a coupling flange of the mixing nozzle.

A device described in DE-100 38 882 A1 has a frame-like slide which can be displaced in linear guides of a coupling plate placed on the tube-like outlet connection piece of the containers, wherein the respective end stop indicates an opened or closed position. In this document reference is made to the advantage of a short force transfer path from the bearing to the clamping plane of the mixing nozzle holder.

All the systems mentioned above for fixing the mixing nozzles in or at outlet orifices which are sufficiently separated from each other have the disadvantage of an attachment element which has to be produced and mounted separately.

In contrast, it is the object of the present invention to provide an improved dispensing device which is simpler to produce and operate.

SUMMARY OF THE INVENTION

A dispensing device for fluid substances in accordance with the invention, which has a receiving element to receive fluid substances having at least two containers which are fixedly connected to each other and have adjacent outlet orifices on the end face, a mixing nozzle which is connected to the receiving element by means of a mixing nozzle holder and is connected to the outlet orifices in a fluid-conducting manner, and a pressure-producing means for ejecting the fluid substances through the outlet orifices, is characterised in that the mixing nozzle holder is a releasable latch closure. A piston, compressed air or the like, for example, is used in a conventional manner as the pressure-producing means.

In one advantageous embodiment of the invention the latch closure is attached to the receiving element. The receiving element and latch closure can thus be formed as one piece.

The latch closure attached to the receiving element preferably has at least one spring arm which can be deformed elastically by exertion of sufficient mechanical pressing force and which has a projection formed thereon which comes into undercut engagement with the mixing nozzle. For this purpose the mixing nozzle has a structural element suitable for undercut engagement of the projection, for example a depression.

In addition, the latch closure can have at least one substantially non-deformable latch element with a projection formed thereon for undercut engagement with the mixing nozzle. The substantially non-deformable latch element thus engages into a structural element of the mixing nozzle which is suitable for undercut engagement. This structural element can the same as during engagement of the elastically deformable spring arm [sic]. The latch closure is released by exerting mechanical pressure on the elastically deformable spring arm. The non-deformable latch element forms a rigid counter-bearing with respect to the elastically deformable spring arm.

Furthermore, the latch closure can have at least one plastically deformable latch element with a projection formed thereon for undercut engagement with the mixing nozzle and/or can have a latch element which breaks when a sufficient mechanical pressing force is exerted and which has a projection formed thereon for undercut engagement with the mixing nozzle. These latch elements can engage into the same structural element as the elastically deformable spring arm. In this case the latch closure is only intended for single use since the elastically deformed or broken latch elements do not generally permit repeated use.

In a further advantageous embodiment of the invention the latch closure is attached to the mixing nozzle. The mixing nozzle or mixing nozzle housing and latch closure can be formed as one piece.

The latch closure attached to the mixing nozzle preferably has at least one spring arm which can be deformed elastically by exertion of a sufficient mechanical pressing force and which has a projection formed thereon which comes into undercut engagement with the receiving element. For this purpose the receiving element has a structural element suitable for undercut engagement of the projection, for example a depression.

In addition, the latch closure can have at least one substantially non-deformable latch element with a projection formed thereon for undercut engagement with the receiving element. The substantially non-deformable latch element thus engages in a structural element of the receiving element suitable for undercut engagement. This structural element can the same as during engagement of the elastically deformable spring arm [sic]. The latch closure is released by exerting mechanical pressure on the elastically deformable spring arm. The non-deformable latch element forms a rigid counter-bearing with respect to the elastically deformable spring arm.

Furthermore, the latch closure can have at least one plastically deformable latch element with a projection formed thereon for undercut engagement with the receiving element and/or a latch element which breaks when a sufficient mechanical pressing force is exerted and which has a projection formed thereon for undercut engagement with the receiving element. These latch elements can engage into the same structural element as the elastically deformable spring arm. In this case the latch closure is only intended for single use since the elastically deformed or broken latch elements do not generally permit repeated use.

In the case of a further advantageous embodiment of the invention the mixing nozzle is connected to the receiving element with the aid of a releasable coupling element. The coupling element is thus releasably attached either to the receiving element or to the mixing nozzle; furthermore, the latch closure is attached to the coupling element.

When the coupling element is releasably attached to the receiving element, the coupling element is connected to the mixing nozzle via the releasable latch closure. When the coupling element is releasably attached to the mixing nozzle the coupling element is connected to the receiving element via the releasable latch closure.

In each of the two cases the coupling element can be formed as one piece with the latch closure.

The latch closure attached to the coupling element preferably has at least one spring arm which is elastically deformable when sufficient mechanical pressing force is exerted and which has a projection formed thereon which comes into undercut engagement with the receiving element or mixing nozzle. For this purpose the receiving element or the mixing nozzle has a structural element suitable for undercut engagement of the projection, for example, a depression.

In addition, the latch closure can have at least one substantially non-deformable latch element with a projection formed thereon for undercut engagement with the receiving element or mixing nozzle. The substantially non-deformable latch element thus engages into a structural element of the receiving element or of the mixing nozzle which is suitable for undercut engagement. This structural element can the same as during engagement of the elastically deformable spring arm [sic]. The latch closure is released in this case by exerting mechanical pressure on the elastically deformable spring arm. The non-deformable latch element forms a rigid counter-bearing with respect to the elastically deformable spring arm.

Furthermore, the latch closure can have at least one plastically deformable latch element with a projection formed thereon for undercut engagement with the receiving element or mixing nozzle and/or a latch element which breaks or deforms plastically when sufficient mechanical pressing force is exerted and which has a projection formed thereon for undercut engagement with the receiving element or mixing nozzle. These latch elements can engage into the same structural element as the elastically deformable spring arm. In this case the latch closure is only intended for single use since the plastically deformed or broken latch elements do not generally permit repeated use.

In the embodiments in accordance with the invention the outlet orifices of the containers are advantageously formed from outlet connection pieces. Furthermore, guide elements can be provided on the receiving element, on the mixing nozzle and/or on the coupling element and facilitate latching of the respective parts to be latched.

BRIEF DESCRIPTION OF THE DRAWINGS

The invention will now be described in more detail with the aid of several exemplified embodiments, wherein reference is made to the attached drawings in which.

DESCRIPTION OF THE PREFERRED EMBODIMENT

Figure 1:
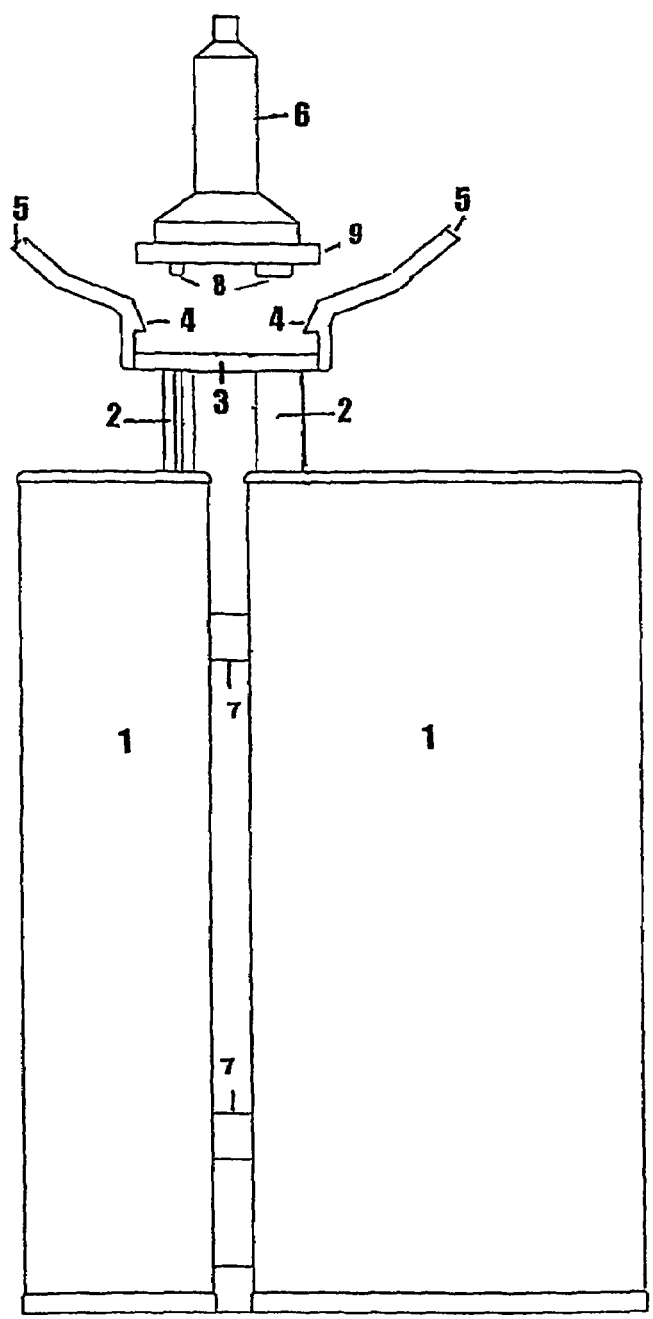
FIG. 1 illustrates a side view (top) and a plan view (bottom) through an embodiment (A) of the dispensing device in accordance with the invention.
Figure 1:
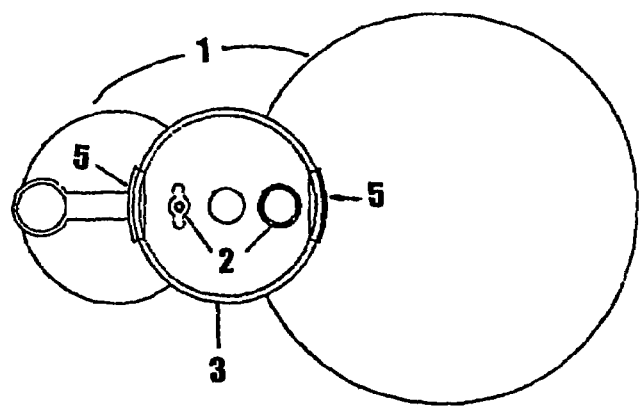

Reference is first made to FIG. 1 which shows a side view (top) and a plan view (bottom) through an embodiment (A) of the dispensing device in accordance with the invention. The dispensing device in accordance with the invention has a receiving element consisting of two containers 1 for receiving fluid substances, and a mixing nozzle 6. The containers 1 connected by struts 7 are provided with outlet connections 2 on the end face, by means of which the fluid substances can be ejected by exertion of suitable pressing force in the direction of the outlet connection pieces. For this purpose the dispensing device cooperates with a pressure-exerting means, for example a pump plunger or a pressure-producing electrical device. The two outlet connection pieces 2 may be connected to each other by means of a stiffening connection element 3, in this case a disc 3. Two elastically deformable spring arms 5 are attached to the disc 3. The spring arms 5 are each attached with one of their ends to the disc 3 in the form of latch levers. Hook-like projections 4 are formed on the spring arms 5 and are suitable for coming into undercut engagement with the mixing nozzle 6. For this purpose the mixing nozzle 6 has a counterpart structure 9 on which the spring arms 5 latch with their hook-like projections. When the mixing nozzle is latched together with the receiving element the mouths 8 of the mixing nozzle 6 produce a fluid-conducting connection with the outlet connection pieces 2 of the containers 1. The spring arms 5 are formed in such a way that they can come into undercut engagement with the counterpart structure 9 only when they are elastically deformed by exertion of mechanical pressure under which the hook-like projections 4 are moved away from each other. In order to attach the mixing nozzle 6 to the receiving element a sufficiently large mechanical pressing force must be exerted on the elastic spring arms 5 against the restoring spring force of the spring arms 5. In this way the latch elements, in this case illustrated as hook-like projections 4, latch behind the counterpart structure 9 of the mixing nozzle 6. By the restoring spring force of the elastic spring arms 5 the latch connection is secured against being released. The latch connection can be released by exertion of a sufficient mechanical pressing force onto the spring arms 5, upon which the hook-like projections 4 are moved away from each other. In order to release the latch closure, an operator can, for example, press the two spring arms 5 apart manually at their free ends. Optionally, the spring arms 5 can be designed to break when sufficient force is applied, the latch closure being intended for a single use only.

Figure 2:
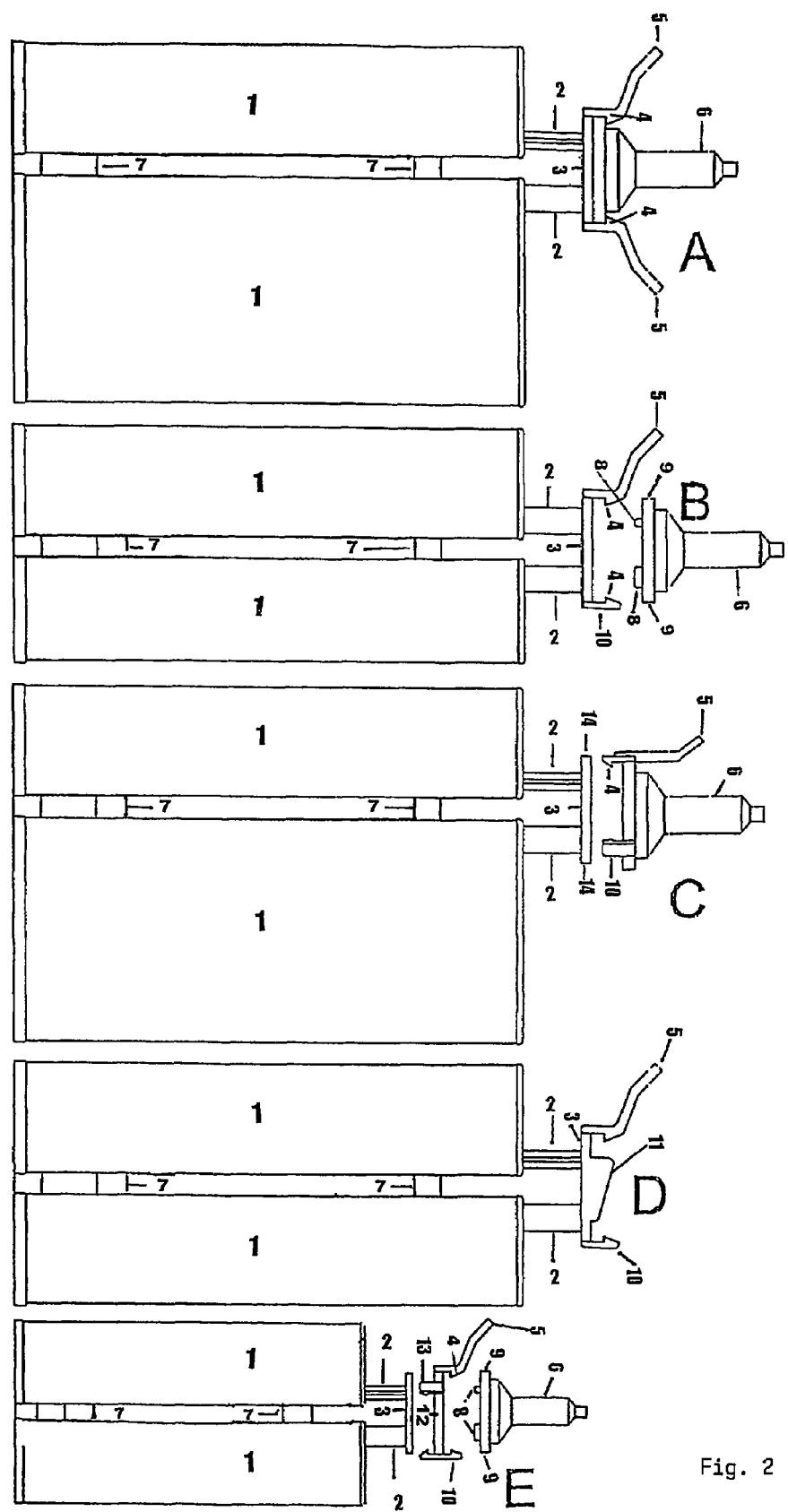
FIG. 2 illustrates in each case a side view (right) and in each case a plan view (left) through four different embodiments (A-E) of the dispensing device in accordance with the invention.

FIG. 2 shows in each case a side view (right) and in each case a plan view (left) through four [sic] different embodiments A-E of the dispensing device in accordance with the invention, wherein embodiment A corresponds to the embodiment shown in FIG. 1. In order to avoid repetition only the differences in the embodiments B-E are illustrated. In the case of the elements of the embodiments B-E which are the same as the elements of the embodiment A reference is made to the statements made in relation thereto.

Embodiment B differs from embodiment A in that instead of two elastically deformable spring arms 5 only a single elastically deformable spring arm 5 and a substantially non-deformable rigid latch element (10) are provided. During latching of the mixing nozzle 6 to the latch closure only the restoring spring force of the individual spring arms must be overcome so that the hook-like projection 4 can move behind the counterpart structure 9 of the mixing nozzle 6. This also applies for release of the latch closure which can be effected, for example, by exertion of a manual pressing force onto the free end of the spring arm 5 against its restoring spring force. Like the spring arm 5 the rigid latch element 10 engages behind the counterpart structure 8 of the mixing nozzle 6. Undesired release of the latch connection is ensured [sic] by the restoring spring force of the spring arm 5.

In embodiment C the latch closure is not attached to the receiving element, as in the embodiments A and B, but to the mixing nozzle 6. The latch closure has an individual spring arm 5 with a hook-like projection 4 formed thereon. A rigid latch element 10 is provided as a counterpart piece to the spring arm 5. The spring arm 5 and latch element 10 engage in the latching position of the latch closure behind the disc 3 connecting the outlet connection pieces 2. By reason of the arrangement of the hook-like projection 4 with respect to the spring arm 5, which differs from the embodiments A and B, the latch connection is released by the spring arm 5 being pressed in the direction of the mixing nozzle with sufficient pressing force to release the latch connection.

Embodiment D corresponds to embodiment B with the exception that, in addition, a guide element 11 for facilitating latching of the mixing nozzle to be latched is provided. The guide element 11 can also be provided on the mixing nozzle or the coupling element 12 shown in embodiment E.

In embodiment E the receiving element is connected to the mixing nozzle 6 by means of a coupling element 12. The coupling element 12 has the two latch elements 10 and 13 for connection to the receiving element, which latch elements come into undercut engagement with the disc 3 during latching. Furthermore, the latch closure for attachment of the mixing nozzle 6 is provided on the coupling element 12. For this purpose the elastically deformable spring arm 5 and the rigid latch element 10 are provided on the coupling element 12. The latch element 10 has two opposing latch lugs since it also serves for attaching the coupling element 12 to the receiving element. The coupling element could be attached in a symmetrical manner to the mixing nozzle, wherein the receiving element is then connected to the coupling element via the latch closure.

Figure 3:
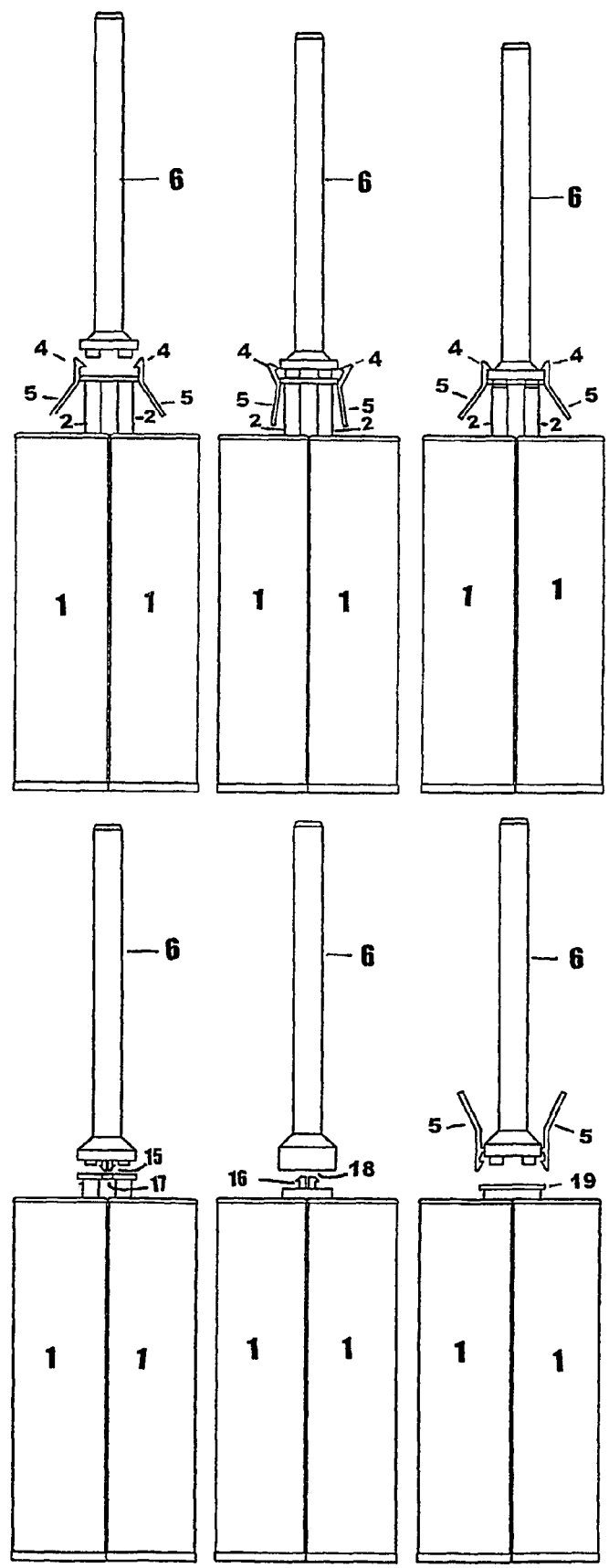
FIG. 3 illustrates respectively a side view through an embodiment (A) of the dispensing device in accordance with the invention in three different states during latching (top), and respectively a side view through three different embodiments of the dispensing device in accordance with the invention (bottom).

In the upper images FIG. 3 shows in each case a side view through embodiment A of the dispensing device in accordance with the invention in three different states during latching. In the left image the state prior to latching is shown. In the middle image the state is shown in which the two elastically deformable spring arms 5 are pressed apart from each other by the counterpart structure of the mixing nozzle 6 against the restoring spring force so that the hook-like projections 4 come into undercut engagement with the mixing nozzle. In the right-hand image the latched state of the mixing nozzle and receiving element is illustrated in which the hook-like projections 4 engage behind the counterpart structure of the mixing nozzle 6.

In the lower images of FIG. 3 in each case a side view through three different embodiments of the dispensing device in accordance with the invention is shown prior to latching. The left-hand lower image shows an embodiment in which the elastically deformable spring arms 15 are disposed between the mouths of the mixing nozzle 6, wherein the hook-like projections of the spring arms 15 face away from each other in contrast to the previous embodiments. The spring arms 15 must accordingly be pressed together against a restoring spring force in order to latch the mixing nozzle with the receiving element. The spring arms 15 engage into a corresponding counterpart structure 17 between the two outlet connection pieces of the containers.

In the central lower image an embodiment is shown in which the spring arms 16, which are identical to the embodiment otherwise shown in the left lower image, are disposed on the receiving element. These engage into a corresponding counterpart structure 18 of the mixing nozzle 6.

In the right-hand lower image an embodiment is shown in which the two elastically deformable spring arms 5, which are attached to the mixing nozzle 6, engage behind a disc-like structure 19 of the receiving element.

The invention claimed is:
1. Dispensing device for fluid substances, comprising:
a receiving element to receive fluid substances, having at least two containers which are fixedly connected to each other and have adjacent outlet orifices on an end face thereof;
a pressure-producing means for ejecting the fluid substances through the outlet orifices; and
a mixing nozzle which is connected to the receiving element by means of a mixing nozzle holder and connected to the outlet orifices in a fluid-conducting manner;

the mixing nozzle holder comprising a releasable latch closure attached to the receiving element, the latch closure comprising two elastically deformable spring arms, each said spring arm having a proximal end at which the spring arm is attached to the receiving element and a free, distal end, each said spring arm having a projection formed thereon adjacent the proximal end for undercut engagement with the mixing nozzle, the projection forming a rigid counter-bearing with respect to the elastically deformable spring arm, wherein the latch closure is formed as one piece with the receiving element.

2. Dispensing device as claimed in claim 1, wherein the latch closure has at least one latch element with a projection formed thereon for undercut engagement with the mixing nozzle, which said at least one latch element breaks when a sufficient mechanical pressing force is exerted.

3. Dispensing device as claimed in claim 1, wherein the outlet orifices are formed as outlet connection pieces.

4. Dispensing device as claimed in claim 1, wherein the outlet orifices are connected to a stiffening connection element.

5. Dispensing device for fluid substances, comprising:
a receiving element to receive fluid substances, having at least two containers which are fixedly connected to each other and have adjacent outlet orifices on an end face thereof;
a pressure-producing means for ejecting the fluid substances through the outlet orifices; and
a mixing nozzle which is connected to the receiving element by means of a mixing nozzle holder and connected to the outlet orifices in a fluid-conducting manner;
the mixing nozzle holder comprising a releasable latch closure attached to the receiving element,
wherein the latch closure attached to the receiving element comprises two elastically deformable spring arms, each said spring arm having a proximal end at which the spring arm is attached to the receiving element and a free, distal end, each said spring arm having a projection formed thereon for undercut engagement with the mixing nozzle, the projection forming a rigid counter-bearing with respect to the elastically deformable spring arm.

6. Dispensing device as claimed in claim 5, wherein the latch closure has at least one latch element with a projection formed thereon for undercut engagement with the mixing nozzle, which said at least one latch element breaks when a sufficient mechanical pressing force is exerted.

7. Dispensing device as claimed in claim 5, wherein the outlet orifices are formed as outlet connection pieces.

8. Dispensing device as claimed in claim 5, wherein the outlet orifices are connected to a stiffening connection element.

* * * * *